(12) United States Patent
Phelps et al.

(10) Patent No.: US 6,475,210 B1
(45) Date of Patent: Nov. 5, 2002

(54) LIGHT TREATMENT OF VULNERABLE ATHEROSCLEROSIS PLAQUE

(75) Inventors: David Y. Phelps, Ancitorace; Gregory Furnish, Louisville, both of KY (US)

(73) Assignee: MedVenture Technology Corp, Louisville, KY (US)

( * ) Notice: Subject to any disclaimer, the term of this patent is extended or adjusted under 35 U.S.C. 154(b) by 0 days.

(21) Appl. No.: 09/502,265

(22) Filed: Feb. 11, 2000

(51) Int. Cl.[7] ................................ A61B 18/18
(52) U.S. Cl. .............. 606/7; 606/13; 606/14; 606/15; 128/898
(58) Field of Search ............... 606/7, 13–16, 606/43, 46, 159.31; 607/89, 100; 128/898, 899

(56) References Cited

U.S. PATENT DOCUMENTS

| | | | | |
|---|---|---|---|---|
| 4,729,384 A | * | 3/1988 | Bazenet | 128/691 |
| 5,254,112 A | * | 10/1993 | Sinofsky et al. | 606/7 |
| 5,470,330 A | * | 11/1995 | Goldenberg et al. | 606/7 |
| 5,924,997 A | * | 7/1999 | Campbell | 600/549 |
| 5,928,222 A | * | 7/1999 | Kleinerman | 606/16 |
| 5,976,496 A | * | 11/1999 | Dean et al. | 424/1.69 |
| 6,063,093 A | * | 5/2000 | Winston et al. | 606/108 |
| 6,228,109 B1 | * | 5/2000 | Tue et al. | 607/113 |
| 6,165,128 A | * | 12/2000 | Ce'spedes et al. | 600/463 |
| 6,179,858 B1 | * | 1/2001 | Squire et al. | 606/198 |
| 6,245,026 B1 | * | 6/2001 | Campbell et al. | 600/549 |

\* cited by examiner

*Primary Examiner*—Linda C. M. Dvorak
*Assistant Examiner*—Ahmed Farah
(74) *Attorney, Agent, or Firm*—Don Halgren

(57) ABSTRACT

A vulnerable plaque treatment catheter arrangement for the analysis and treatment of the lipid pool of a vulnerable plaque in a coronary artery is disclosed. The arrangement comprises a flexible, elongated, hollow sheath having a proximal end and a distal end, the sheath being arranged for insertion into a coronary artery. A first energy emitter and receiver device is arranged in an annular array in the distal end of the sheath. An energy generator source and an energy control unit is arranged in communication with the first device to provide both diagnosis and treatment to vulnerable plaque within a coronary artery.

11 Claims, 1 Drawing Sheet

LIGHT TREATMENT OF VULNERABLE ATHEROSCLEROSIS PLAQUE

BACKGROUND OF THE INVENTION

1. Field of the Invention

This invention relates to the treatment of vulnerable atherosclerosis and more particularly to the treatment of a lipid pool using light energy, within a coronary artery.

2. Prior Art

Treating atherosclerosis is a difficult procedure, because locating the source of the problem and then curing that problem involves sophisticated analysis and treatment of this coronary artery disease which may otherwise be called heart disease. It is the leading killer of men and women in the world today. It is characterized by deposits of fat, fibrin, cellular debris and calcium on the inside of arterial walls. The early stages of atherosclerotic development is believed to occur as damage to the endothelial cells and tunica intima of the vessel wall. Once this damage has begun, the endothelial cells proliferate and attract a build-up of lipid substances. When these coronary arteries become blocked, symptoms ranging from angina to heart attacks, may occur. In a percentage of these cases, the coronary arteries may be unblocked through a non-invasive technique such as balloon angioplasty. Some five hundred to six hundred thousand angioplasties are performed each year within the United States. Where balloon angioplasty may not be appropriate, a bypass of the occluded or blocked vessel may be necessary. Identifying an opening such occlusions is known to give relief to the symtoms of angina, but it is also known that they do little to prolong life expectancy. The real killer in this coronary artery disease is often sudden blockages that are caused not by the slow accumulation of plaque that gradually block off the arteries, but by a sudden thrombosis (clotting) of the arteries caused by what are now referred to as "vulnerable plaque".

Vulnerable plaques are defined as plaques prone, in the presence of an appropriate trigger, to events such as ulceration rupture, erosion or thrombus that can lead to an acute syndrome. Those events are believed to share three common characteristics, a large lipid pool, a thin fibrous cap and macrophage infiltration.

Present methods of diagnosing arterial disease, using such as stress tests as angiograms, are inadequate at detecting these "vulnerable plaques". Therefore, in most instances, this potentially lethal condition often goes untreated.

It is an object of the present invention to provide analysis and treatment options for this particular condition.

It is a further object of the present invention to provide a plaque treatment utilizing an improved catheter apparatus to identify and treat lipid accumulation by multiplexing components and utilizing sequential operations of those components within the small space of the catheter within an artery.

BRIEF SUMMARY OF THE INVENTION

The present invention relates to a diagnostic and treatment catheter for control of vulnerable atherosclerosis plaque within a coronary artery. The diagnostic and treatment catheter of the present invention is arranged to be pushed into a coronary artery, in search of and to treat vulnerable plaques, which are defined as plaques prone, in the presence of an appropriate trigger, to events such as ulceration, rupture, erosion or thrombus that may lead to an acute syndrome. Such vulnerable plaques are characterized by a large lipid pool, a thin fibrous cap and macrophage infiltration. The diagnostic and treatment catheter of the present invention is arranged to search for such plaques, through spectrographic identification. This diagnostic and treatment catheter is comprised of an elongated polymeric or elastomeric sheath, sized for coronary artery insertion. The elongated diagnostic and treatment catheter has a distal end with an annular array of energy emitters arranged for the transmission of energy through the wall of the catheter sheath. The annular array of energy emitters are in communication with a energy source through a cable or optical fiber connected therebetween. In one of the preferred embodiments, the energy or light source has an energy or light control unit to govern the frequency and intensity of the energy or light emitted by the energy or light emitters.

In a further preferred embodiment of the present invention, the annular array of energy or light emitters also comprises an annular array of energy or light sensors so as to receive the energy or light reflected back from a fibrous cap and lipid pool, thus distinguished thereby by its spectrographic contrast to an adjacent arterial wall or to a pre-determined spectographic configuration matched-up within the memory of its control unit. The energy or light treatment emitted by the energy or light emitters may be in the ultrasonic or infrared range so as to alter the lipid pool either through shrinking, congealing, or other effects. Upon spectrographic identification of a vulnerable plaque, the energy or light source control unit may signal an audible or visual alarm, or be arranged to automatically provide such a higher energy or light frequency or intensity level than that which was used for the identification process, so as to treat the vulnerable plaque into shrinking, congealing or otherwise becoming innocuous.

The treatment process may then be followed with a further diagnostic spectrographic identification process to determine the efficacy of the light or energy treatment of that vulnerable plaque. Should the spectrographic analysis determine further treatment is necessary, the light control unit will signal the energy or light source to again ramp up to the required energy level or intensity for a subsequent treatment thereof.

In a further preferred embodiment of the present invention, an annular array of independent sensors may be disposed longitudinally adjacent the annular array of energy or light emitters, disposed within the catheter sheath. These independent sensors are in communication with an independent sensor control unit. The independent sensor control unit is in communication with the energy or light control unit to effect subsequent treatment processes upon the lipid pool/vulnerable plaque.

In operation, energy from the energy or light emitters would be received in the sensors after that energy was received by the vulnerable plaque, that is, the fibrous cap and lipid pool thereadjacent. The sensors would communicate, through optical fibers, or circuit means, to the independent sensor control unit to effectively regulate the energy light control unit and regulate the frequency and intensity of the energy light source of the energy or light emitters. The energy emitted may be in the microwave range, the ultrasound range or the infrared range and the light may also be in the ultraviolet range or emitted as a tunable laser light.

The invention thus comprises a vulnerable plaque treatment catheter arrangement for the analysis and treatment of the lipid pool of a vulnerable plaque in a coronary artery, comprising: a flexible, elongated, hollow sheath having a proximal end and a distal end, the sheath arranged for insertion into a coronary artery, an energy emitter and receiver device arranged in an annular array in the distal end of the sheath, an energy generator source and an energy control unit in communication with the device to provide a diagnosis and treatment to vulnerable plaque within a coronary artery. The device may emit infrared radiation onto the vulnerable plaque in the artery. The device may emit ultrasound radiation onto the vulnerable plaque in the artery. The device may emit laser light onto the vulnerable plaque in the artery. The energy emitter may comprise an annular array of emitting devices and the energy receiver may comprise a separate annular array of receiving sensors longitudinally spaced apart in the sheath from the emitting devices.

The invention may also include a method of treating vulnerable plaque in a coronary artery by a vulnerable plaque catheter, comprising the steps of: placing an array of energy emitting devices in a distal end of a sheath of the catheter, connecting the energy emitting devices, via a communication line, to an energy generating source, actuating the energy emitting devices through a first signal from a control unit, so as send an initial scanning discharge of energy from the devices to analyze the internal wall of the artery, receiving a return of the initial energy discharge to analyze the internal wall of the coronary artery, actuating the energy emitting devices through a second signal from the control unit, to generate an increased treating-energy emission from the devices, so as to treat vulnerable plaque discovered in the artery. The method may also include re-actuating the energy emitting devices to do a second scanning discharge of energy from the energy emitting devices to determine the effectiveness of the treating-energy discharge on the vulnerable plaque. The energy discharged may comprise infrared light. The energy discharged may comprise laser light. The energy discharged may comprise ultrasonic energy. The control unit is arranged to complete a spectrographic analysis to determine the effectiveness of the first scanning energy emission from the energy emitting devices. The method may include arranging an array of independent sensors adjacent said array of emitting devices, to function to receive energy from the vulnerable plaque, for forwarding to an independent sensor unit to further control the energy emitting generator source.

The invention may also comprise a method of treating vulnerable plaque in a wall of a coronary artery by a vulnerable plaque catheter, comprising the steps of: energizing an array of first devices in a distal end of a sheath of a coronary catheter so as to emit a first level of energy in a coronary artery, to scan for vulnerable plaque in said artery; receiving the return of the first level of energy from the wall of the coronary artery, in a energy control unit in communication with the first devices; analyzing the first level of energy returned by the energy control unit; and actuating the first devices to a higher second level of energy output therefrom upon the energy control unit determining a vulnerable plaque exists on the wall of the artery. The method may also comprise the steps of re-energizing the first devices to evaluate the effectiveness of the second level of energy applied to the vulnerable plaque, re-actuating the first energy devices to the second level of energy discharge upon subsequent determination of further treatment needed by the control unit.

Thus what has been shown is a vulnerable plaque treatment catheter which is providing a energy or light delivered to a target such as vulnerable plaque for a first spectrographic analysis thereof, and then a subsequent treatment of that target entity should vulnerable plaque be identified therein. The treatment would preferably be effected by the same energy or light source and energy light emitters that were used as the diagnostic indicators.

BRIEF DESCRIPTION OF THE DRAWINGS

The objects and advantages of the present invention will become more apparent, when viewed in conjunction with the following drawings in which.

DESCRIPTION OF THE PREFERRED EMBODIMENTS

Figure 1:
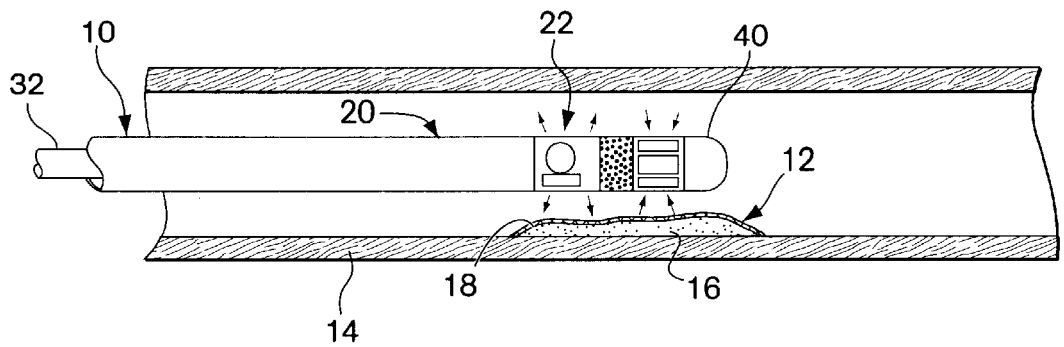
FIG. 1 is a side elevational view of a portion of a diagnostic end treatment catheter within a coronary artery.
Figure 2:
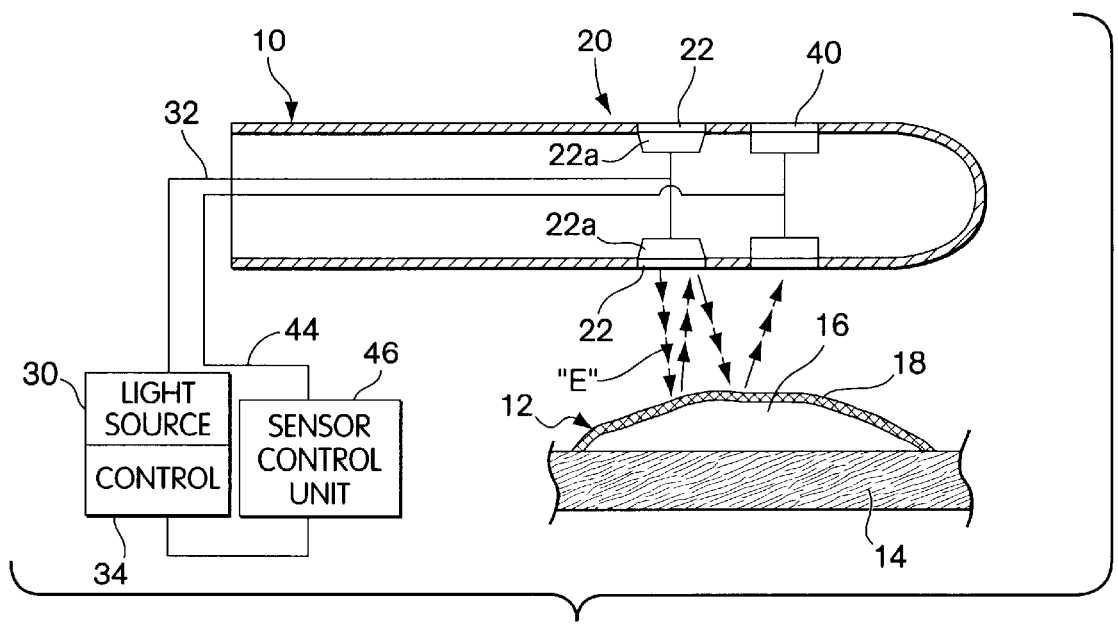
FIG. 2 is a side elevational view, in section, together with a block diagram of the circuit, of the diagnostic and treatment catheter shown in FIG. 1.

Referring now to the drawings in detail, and particularly to FIG. 1, there is shown the present invention which comprises a diagnostic and treatment catheter 10 for control of vulnerable atherosclerosis plaque 12 within a coronary artery 14. The diagnostic and treatment catheter 10 of the present invention is arranged to be pushed into the coronary artery 14, in search of and to treat vulnerable plaques 12, which are defined as plaques prone, in the presence of an appropriate trigger, to events such as ulceration, rupture, erosion or thrombus that may lead to an acute syndrome. Such vulnerable plaques 12 are characterized by a large lipid pool 16, a thin fibrous cap 18 and macrophage infiltration. The diagnostic and treatment catheter 10 of the present invention is arranged to search for such plaques, through spectrographic or echo identification. This diagnostic and treatment catheter a distal portion of which is shown in section in FIG. 2, is sized for coronary artery insertion. The elongated diagnostic and treatment catheter 10 has a distal end 20 with an annular array of energy emitter devices 22 arranged for the transmission of energy through the wall of the catheter sheath 14. The annular array of energy emitter devices 22 are in communication with an energy source 30 through a cable, flexible waveguide or optical fiber 32 connected therebetween. In one of the preferred embodiments, the energy or light source 30 has an energy or light control unit 34 to govern the frequency and intensity of the energy or light "E" emitted by the energy or light emitter devices 22.

In a further preferred embodiment of the present invention, the annular array of energy or light emitter devices 22 also comprises, as double duty, an annular array of energy or light sensors 22a, (i.e. photoelectric detectors, piezo electric units or the like), so as to also receive the energy or light "E" reflected back from a fibrous cap 18 and lipid pool 16, thus distinguished thereby in the energy/light control unit 34 by its spectrographic contrast or echo pattern to an adjacent arterial wall or to a pre-determined spectrographic configuration or echo pattern match-up or the like within the memory of its control unit 34. The energy or light treatment "E" emitted by the energy or light emitter devices 22 may preferably be in the ultrasonic or infrared range so as to be able to alter the lipid pool 16 either through shrinking, congealing, or other effects. Upon such identification of a vulnerable plaque, the energy or light source control unit 34 may signal an audible or visual alarm, or be arranged to automatically provide such a higher energy or light frequency or intensity level than that which was used for the identification process, so as to treat the vulnerable plaque 12 into shrinking, congealing or otherwise becoming innocuous.

The treatment process may then be followed with a further diagnostic spectrographic, echo or energy absorption identification process to determine the efficacy of the light or energy treatment of that vulnerable plaque. Should the diagnostic analysis determine further treatment is necessary, the light control unit 34 will signal the energy or light source 30 (i.e. laser, ultrasound or the like) to again ramp up to the required energy level or intensity for a subsequent treatment thereof.

In a further preferred embodiment of the present invention, an annular array of independent sensors 40 may be disposed longitudinally adjacent the annular array of energy or light emitter/sensor devices 22 and 22a, disposed within the catheter sheath 14. These independent sensors 40 may be in communication with an independent sensor control unit 44 via a cable or optic fiber 46. The independent sensor control unit is in communication with the energy or light control unit 34 to effect subsequent treatment processes upon the lipid pool/vulnerable plaque.

In operation, energy "E" from the energy or light emitters would be received in the independent sensors 40 after that energy "E" was received and effected by the vulnerable plaque 12, that is, the fibrous cap 18 and lipid pool 18 thereadjacent. The independent sensors 40 would communicate, through the optical fibers, or circuit means 44 to the independent sensor control unit 46 to effectively regulate the energy light control unit 34 and regulate the frequency and intensity of the energy light source 30 of the energy or light emitter devices 22. The energy "E" emitted may be in the microwave range, the ultrasound range or the infrared range and the light may also be in the ultraviolet range or emitted as a tunable laser light.

Thus what has been shown is a vulnerable plaque treatment catheter which is providing a energy or light delivered to a target such as vulnerable plaque for a first spectrographic, echo or reflective analysis thereof, and then a subsequent treatment of that target entity should vulnerable plaque be identified therein. The treatment in the preferred embodiment would preferably be effected by the same energy or light source and energy light emitters that were used as the diagnostic indicators.

We claim:

1. A vulnerable plaque treatment catheter arrangement for the analysis and treatment of the lipid pool of a vulnerable plaque in a coronary artery, comprising:
   a flexible, elongated, hollow sheath having a proximal end and a distal end, said sheath arranged for insertion into a coronary artery;
   an energy emitter and an energy receiver device arranged in an annular array in said distal end of said sheath, wherein said energy emitter comprises an annular array of emitting devices and said energy receiver comprises a separate annular array of receiving sensors longitudinally spaced apart in said sheath from said emitting devices wherein said sensors receive signals from oblique angles;
   an energy generator source and an energy control unit in communication with said device to provide a diagnosis and treatment to vulnerable plaque within a coronary artery.

2. The vulnerable plaque treatment catheter arrangement as recited in claim 1, wherein said device emits infrared radiation onto said vulnerable plaque in said artery.

3. The vulnerable plaque treatment catheter arrangement as recited in claim 1 wherein said device emits ultrasound radiation onto said vulnerable plaque in said artery.

4. The vulnerable plaque treatment catheter arrangement as recited in claim 1, wherein said device emits laser light onto said vulnerable plaque in said artery.

5. A method of treating vulnerable plaque in a coronary artery by a vulnerable plaque catheter, comprising the steps of:
   placing an array of energy emitting and energy receiving devices in a distal end of a sheath of said catheter;
   connecting said energy emitting devices, via a communication line, to an energy generating source, wherein said energy emitter comprises an annular array of emitting devices and said energy receiver comprises a separate annular array of receiving sensors longitudinally spaced apart in said sheath from said emitting devices wherein said sensors receive signals from oblique angles;
   actuating said energy emitting devices through a first signal from a control unit, so as to send an initial scanning discharge of energy from said devices to analyze the internal wall of said artery;
   receiving a return of said initial energy discharge to analyze the internal wall of said coronary artery;
   actuating said energy emitting devices through a second signal from said control unit, to generate an increased treating-energy emission from said devices, so as to treat vulnerable plaque discovered in said artery.

6. The method of treating vulnerable plaque in a coronary artery by a vulnerable plaque catheter, as recited in claim 5, including the step of:
   re-actuating said energy emitting devices to do a second scanning discharge of energy from said energy emitting devices to determine the effectiveness of said treating-energy discharge on said vulnerable plaque.

7. The method of treating vulnerable plaque in a coronary artery by a vulnerable plaque catheter, as recited in claim 6, wherein said energy discharged comprises infrared light.

8. The method of treating vulnerable plaque in a coronary artery by a vulnerable plaque catheter, as recited in claim 6, wherein said energy discharged comprises laser light.

9. The method of treating vulnerable plaque in a coronary artery by a vulnerable plaque catheter as recited in claim 6, wherein said energy discharged comprises ultrasonic energy.

10. The method of treating vulnerable plaque in a coronary artery by a vulnerable plaque catheter as recited in claim 6, wherein said control unit completes a spectrographic analysis to determine the effectiveness of said first scanning energy emission from said energy emitting devices.

11. The method of treating vulnerable plaque in a coronary artery by a vulnerable plaque catheter as recited in claim 6, including the step of:
   arranging an array of independent sensors adjacent said array of emitting devices, to function to receive energy from said vulnerable plaque, for forwarding to an independent sensor unit to further control said energy emitting generator source.

* * * * *